(12) United States Patent
Anderson et al.

(10) Patent No.: US 7,540,906 B2
(45) Date of Patent: Jun. 2, 2009

(54) METAL SALTS OF HYDROLYZED OLEFIN/MALEIC ANHYDRIDE COPOLYMERS AND THEIR USE AS WOOD PRESERVATIVES

(75) Inventors: Albert Gordon Anderson, Wilmington, DE (US); John Feaster, Chesapeake City, MD (US); Damini Patel, Wallingford, PA (US); Mark Scialdone, West Grove, PA (US)

(73) Assignee: E.I. Du Pont de Nemours & Company, Wilmington, DE (US)

( * ) Notice: Subject to any disclaimer, the term of this patent is extended or adjusted under 35 U.S.C. 154(b) by 27 days.

(21) Appl. No.: 11/643,598

(22) Filed: Dec. 21, 2006

(65) Prior Publication Data

US 2007/0163465 A1      Jul. 19, 2007

Related U.S. Application Data

(60) Provisional application No. 60/755,211, filed on Dec. 30, 2005.

(51) Int. Cl.
| | |
|---|---|
| A01N 59/20 | (2006.01) |
| A01N 59/16 | (2006.01) |
| A01P 3/00 | (2006.01) |
| A01P 7/04 | (2006.01) |
| B05D 5/00 | (2006.01) |
| B05D 7/06 | (2006.01) |
| B05D 1/02 | (2006.01) |
| B05D 1/18 | (2006.01) |
| B05D 1/28 | (2006.01) |
| B32B 21/04 | (2006.01) |
| B32B 21/06 | (2006.01) |
| A01N 35/06 | (2006.01) |

(52) U.S. Cl. ............ 106/18.32; 106/15.05; 424/78.08; 424/78.09; 427/297; 427/351; 427/389.9; 427/391; 427/392; 427/393; 427/421.1; 427/428.01; 427/439; 427/440; 428/375; 428/532; 428/537.1; 428/537.5; 514/492; 514/494; 514/500; 514/772; 514/772.3

(58) Field of Classification Search .............. 106/15.05, 106/18.32; 424/78.08, 78.09, 351, 440; 427/297, 427/389.9, 391, 392, 393, 421.1, 428.01, 427/439; 428/532, 537.1, 537.5, 375; 514/492, 514/494, 500, 772, 772.3
See application file for complete search history.

(56) References Cited

U.S. PATENT DOCUMENTS

| | | | |
|---|---|---|---|
| 3,404,135 A | 10/1968 | Wolfgang | |
| 3,706,704 A | 12/1972 | Heilman et al. | |
| 4,175,090 A | 11/1979 | Berry | |
| 4,409,358 A | 10/1983 | Kraft et al. | |
| 4,504,468 A | 3/1985 | Brill et al. | |
| 4,656,192 A | 4/1987 | Yamato | |
| 4,737,491 A * | 4/1988 | Leppavuori et al. | 424/78.18 |
| 4,988,545 A | 1/1991 | Laks | |
| 5,242,685 A | 9/1993 | Ruppersberger et al. | |
| 6,197,763 B1 | 3/2001 | Thompson et al. | |
| 6,541,038 B1 | 4/2003 | Tanaka et al. | |
| 6,787,675 B2 | 9/2004 | Pan et al. | |
| 6,843,837 B2 | 1/2005 | Zhang et al. | |
| 6,924,398 B2 | 8/2005 | Pan et al. | |
| 6,978,724 B2 | 12/2005 | Anderson | |
| 7,259,187 B2 | 8/2007 | Kagechika | |
| 2004/0089196 A1 | 5/2004 | Anderson et al. | |
| 2005/0000387 A1 | 1/2005 | Wang et al. | |
| 2005/0107467 A1 | 5/2005 | Richardson | |
| 2007/0157847 A1 | 7/2007 | Anderson et al. | |
| 2007/0163465 A1 | 7/2007 | Anderson et al. | |
| 2007/0163466 A1 | 7/2007 | Anderson | |
| 2007/0169664 A1 | 7/2007 | Anderson | |

FOREIGN PATENT DOCUMENTS

| | | |
|---|---|---|
| AU | 614386 | 8/1991 |
| EP | 0 728 478 | 8/1968 |
| EP | 0 111 995 A2 | 6/1984 |
| EP | 0 137 126 | 4/1985 |
| EP | 238 413 | 9/1987 |
| EP | 565266 A1 * | 10/1993 |
| FR | 2 668 031 | 4/1992 |
| FR | 2668031 A1 * | 4/1992 |
| JP | 49-055829 | 5/1974 |
| JP | 01-038 203 | 2/1989 |
| JP | 1-299291 A | 12/1989 |
| JP | 02/006402 | 1/1990 |
| JP | 7-69825 A | 3/1995 |
| JP | 7-126111 A | 5/1995 |
| JP | 8-12504 | 1/1996 |
| JP | 09175916 | 7/1997 |
| JP | 10-45518 | 2/1998 |
| JP | 10-291 205 | 11/1998 |
| JP | 2000/141316 | 5/2000 |
| JP | 2001/097808 | 4/2001 |
| JP | 2001-310302 | 11/2001 |
| JP | 2003137702 | 5/2003 |
| JP | 2003-334804 | 11/2003 |
| JP | 2004-043327 | 2/2004 |
| WO | WO 97/15382 A1 | 5/1997 |

(Continued)

OTHER PUBLICATIONS

U.S. Appl. No. 60/755,213, filed Dec. 30, 2005, Albert Gordon Anderson.

(Continued)

*Primary Examiner*—Anthony J Green (57) ABSTRACT

Complexes of copper and/or zinc with hydrolyzed olefin/maleic anhydride copolymers were solubilized in ammoniacal solution providing preservative solutions that fully penetrate wood. With loss of the ammonia from the wood, the complexes were stably retained in the wood providing a long lasting preservative.

20 Claims, 1 Drawing Sheet

FOREIGN PATENT DOCUMENTS

| WO | WO 00/19827 | 4/2000 |
|---|---|---|
| WO | WO 2004/041491 | 5/2004 |

OTHER PUBLICATIONS

U.S. Appl. No. 60/755,214, filed Dec. 30, 2005, Albert Gordon Anderson.

U.S. Appl. No. 60/755,242, filed Dec. 30, 2005, Albert Gordon Anderson.

W.J. Brill et al., "Termite Killing By Molybdenum and Tungsten Compounds," Naturwissenschaften, vol. 74:494-495 (1987), no month .

Connick et al. "Environmental Entomology", vol. 30, pp. 449-455, no date.

Carol A. Clausen: Report #IRG/WP 96-10160: "Ibuprofen Inhibits In Vitro Growth of Brown-Rot Fungi" International Research Group on Wood Preservation, Stockholm, Sweden (1996), no month.

A. Trinchero et al., "Spectroscopic Behavior of Copper Complexes of Non-Steroidal Antiinflammatory Drugs" Biopolymers, vol. 74, pp. 120-124 (2004), no month.

S. Dutta et al., "Structural Characterization and Sod Activity of Copper-Oxaprozinate," Inorganic Chemistry Communications, Elsevier, Amsterdam, NL, vol. 7, No. 9, pp. 1071-1074 (Sep. 2004).

International Search Report, Application No. PCT/US2006/049543, Written Opinion of the International Searching Authority (Jul. 18, 2007).

International Search Report, Application No. PCT/US2006/049541, Written Opinion of the International Searching Authority (Aug. 20, 2007).

International Search Report, Application No. PCT/US2006/049544, Written Opinion of the International Searching Authority, International Filing Date (Dec. 28, 2006).

International Search Report, Application No. PCT/US2006/049542, Written Opinion of the International Searching Authority (Aug 15, 2007).

Mounir Baya et al., "Fungicidal Activity of Beta-Thujaplicin Analogues," Pest Management Science, vol. 57, pp. 833-838 (2001), no month.

John M. Black, "inorganic Surface Treatments for Weather Resistant Natural Finishes," U.S.D.A. Forrest Service Research Paper 174, vol. 232, p. 40 (1974, no month.

Jennifer Cowan et al., "Leaching studies and fungal resistance of potential new wood preservaties," Institute of Technology and School of Chemical and Biomolecular Engineering, Georgia Institute of Technology, Article No. 9796 (2003), no month.

U.S. Appl. No. 61/014,812, filed Dec. 19, 2007, Albert G. Anderson et al.

U.S. Appl. No. 61/014,820, filed Dec. 19, 2007, Albert G. Anderson et al.

U.S. Appl. No. 61/014,827, filed Dec. 19, 2007, Albert G. Anderson et al.

U.S. Appl. No. 61/014,830, filed Dec. 19, 2007, Albert G. Anderson et al.

U.S. Appl. No. 61/014,841, filed Dec. 19, 2007, Albert G. Anderson et al.

Chemical Abstract No. 47:8673, abstract of an article by Bryant et al entitled "Formation Constants of Some Metal-Tropolone Complexes", Nature (1952), 170, 247-8, no month.

Chemical Abstract No. 47:65435, abstract of an article by Bryant et al entitled "Formation Constants of Metal Complexes of Tropolone and Its Derivatives", Journal of the American Chemical Society (1953), 75, 3784-6, no month.

Chemical Abstract No. 48:41860, abstract of an article by Bryant et al entitled "Formation Constants of Metal Complexes of Tropolone and Its Derivatives", Journal of the American Chemical Society (1954), 76, 1696-7, no month.

\* cited by examiner

ial, and providing an effective preservative composition for
METAL SALTS OF HYDROLYZED OLEFIN/MALEIC ANHYDRIDE COPOLYMERS AND THEIR USE AS WOOD PRESERVATIVES This application claims the benefit of U.S. Provisional Application No. 60/755,211, which is incorporated in its entirety as a part hereof for all purposes.

TECHNICAL FIELD

This invention relates to polymeric binders for fungitoxic and termiticidal salts for use in preservatives for wood and other cellulosic materials. Specifically, protection of the cellulosic materials is provided by the application of solutions of copper or zinc salts of hydrolyzed olefin/maleic anhydride copolymers. These complexes readily penetrate the cellulosic materials.

BACKGROUND

The decay of wood and other cellulosic materials by fungi, and the consumption of wood by termites, cause significant economic loss. Until recently, the most widely used wood preservative has been chromated copper arsenate (CCA). However, production of CCA for use in residential structures was prohibited as of January 2004 due to issues raised concerning the environmental impact and safety of arsenic and chromium used in CCA-treated lumber. As CCA replacements, arsenic-free and chromium-free wood preservatives are sought.

Various alternative approaches have been taken to incorporating copper into wood preservatives. Salts of copper and other fungitoxic metals are generally water soluble, and rapidly leach from treated wood causing loss of the preservative function. Polymeric binders can be used to retain fungitoxic and termiticidal metal complexes in wood. U.S. Pat. No. 6,843,837, for example, discloses a wood preservative containing metals complexed with a non-polymeric amine, a polyethylenimine, and ammonia together with a vinyl based polymer. Such a composition using a nonionic polymer may readily biodegrade due to colonization of wood by soil bacteria, thereby allowing leaching of the protective metal complex from the wood.

US 2004/089,196 discloses a wood preservative containing a copper complex with polymers containing amidoxime, hydroxamic acid, thiohydroxamic acid, N-hydroxyurea, N-hydroxycarbamate, or N-nitrosoalkyl-hydroxylamine that is solubilized using ammonia, ethanolamine, or pyridine.

U.S. Pat. No. 4,737,491 discloses a wood preservative containing copper and/or zinc complexes dissolved in water, and a polyacrylic acid having a molecular weight of less than 2,000, for stabilizing the metal complex in wood. The polyacrylic acid polymer copper complex is soluble in ammonia water, or forms micelles in ammonia water, and penetrates wood at least partly. It is reported by U.S. Pat. No. 4,737,491, however, that polyacrylic acid polymers with molecular weights above 2,000 have low wood penetration, which results in largely or only surface impregnation of the wood for solutions of polymers that have molecular weights above 2,000.

U.S. Pat. No. 4,409,358 discloses a crop protection agent that is a copper amine salt of a polymer or copolymer of acrylic acid and/or methacrylic acid and optionally a lower alkyl ester of acrylic acid or methacrylic acid. U.S. Pat. No. 5,242,685 discloses a crop protection agent for controlling fungi or bacteria that is an aqueous solution of a polymer acid, containing acrylic acid or methacrylic acid and optionally an acrylate or methacrylate, and at least 12% of copper, where the copper is dissolved by applying ammonia gas under pressure. The expense in making acrylic acid or methacrylic acid, and the requirement for 2 moles of monobasic (meth)acrylic acid groups per mole of Cu make this type of agent undesirable for commercial preparation.

U.S. Pat. No. 4,175,090 discloses a process for preparing a solution containing a cuprammonium complex of one or more $C_1$ to $C_4$ monocarboxylic acids. This type of complex would readily leach from treated wood and thus not provide a lasting preservative.

There thus remains a need for wood preservatives that are highly penetrating, effective, long lasting, and easily prepared for replacement of the CCA wood preservative.

SUMMARY

One embodiment of this invention provides an aqueous composition comprising in admixture (a) a complex comprising (i) copper ions, zinc ions or a mixture thereof, and (ii) a hydrolyzed olefin/maleic anhydride copolymer of at least about 2,000 molecular weight; and (b) ammonia and/or ethanolamine; wherein component (b) is present in an amount sufficient to solubilize the complex.

Another embodiment of this invention provides a process for preparing a composition by combining the components (a) and (b) described above, and solubilizing a complex as formed therefrom.

A further embodiment of this invention provides a process for preserving cellulosic material, or an article that comprises cellulosic material, comprising contacting the cellulosic material or article with the composition described above.

Yet another embodiment of this invention provides cellulosic material, or an article comprising cellulosic material, wherein the above described composition is adsorbed on or absorbed in the cellulosic material.

DETAILED DESCRIPTION

Figure 1:
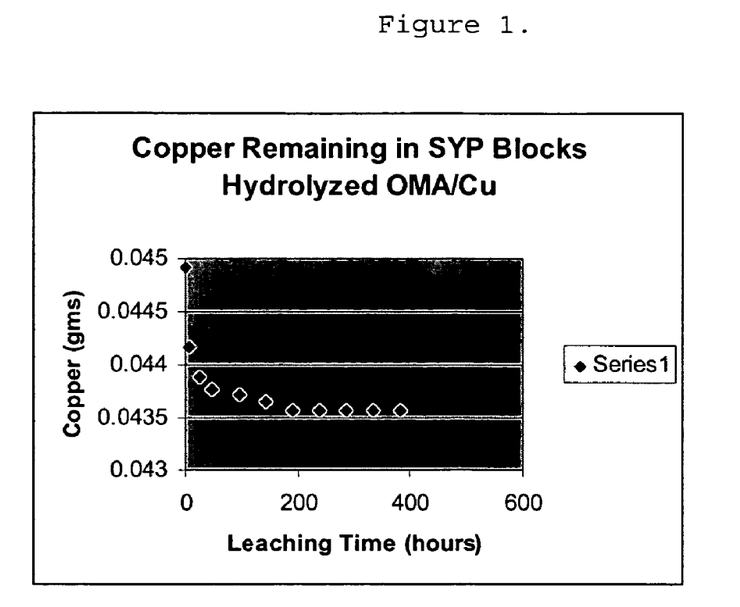
FIG. 1 shows a graph of the amount of copper remaining in a leaching study of wood blocks treated with a solution containing hydrolyzed octene/maleic anhydride copolymer.
Figure 2:
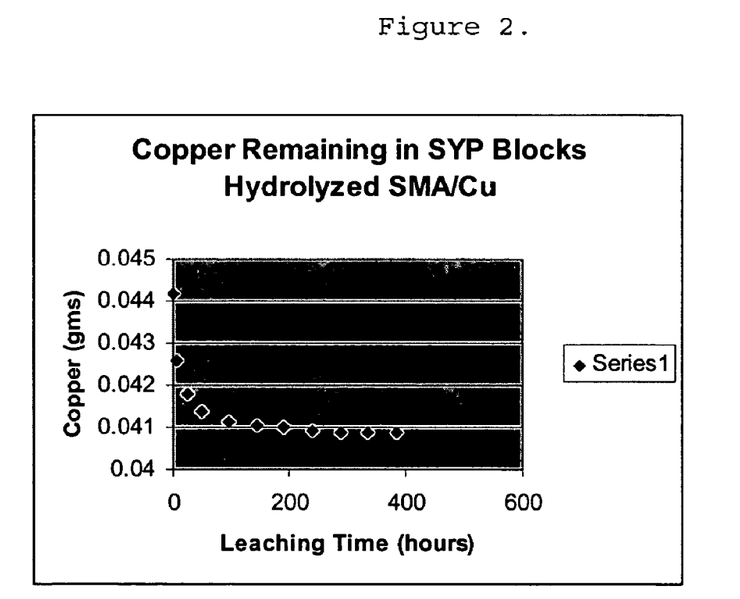
FIG. 2 shows a graph of the amount of copper remaining in a leaching study of wood blocks treated with a solution containing hydrolyzed styrene/maleic anhydride copolymer.

A complex that is formed from a hydrolyzed olefin/maleic anhydride copolymer having a molecular weight in excess of about 2,000, and copper and/or zinc ions, is solubilized by, for example, ammonia or ethanol amine, and is used in such form as a deeply-penetrating and long lasting preservative for wood and other cellulosic materials. As the metal ion complex is solubilized in an aqueous medium, it can be readily adsorbed onto, and/or absorbed or imbibed into, wood or other cellulosic materials. Upon loss or evaporation of the solvent or co-solvents in the solution, the complex becomes insoluble, thereby fixing the hydrolyzed olefin/maleic anhydride copolymer and the metal ion(s) within the target material, and providing an effective preservative composition for the cellulosic material. The hydrolyzed olefin/maleic anhydride copolymer acts as a polymeric binder to retain the copper in or on the cellulosic material.

A cellulosic material is preserved in the sense that contact with a composition of this invention protects the material against decay or deterioration from deleterious effects as caused by either or both of pests and living organisms. For example, a composition of this invention protects a cellulosic material against termite attack, and also provides it with fungal protection, due to the termiticidal activity and the fungicidal activity of the active ingredients of the composition such as the copper and/or zinc. The potential for deterioration or destruction of a cellulosic material by exposure to natural conditions or hazards is thus reduced and preferably prevented by the presence in and/or on the material of a composition of this invention. A process of this invention provides preservation for cellulosic materials by providing contact of the materials with a composition of this invention, and thus achieves the benefits of protection against adverse conditions, pests and organisms, such as termites and fungus as described above.

The cellulosic materials that can be treated with a composition of this invention are those that contain or are derived from cellulose, which is a polysaccharide that forms the main constituent of the cell wall in most plants, and is thus the chief constituent of most plant tissues and fibers. These cellulosic materials include wood and wood products such as lumber, plywood, oriented strand board and paper, in addition to lignin, cotton, hemicellulose and cellulose itself. References herein to the preservation of wood by the use of a composition of this invention, or by the performance of a process of this invention, or references to the usefulness of a composition hereof as a wood preservative, should therefore be understood to be references to the preservation of all types of cellulosic materials, not just wood alone.

Hydrolyzed Olefin/Maleic Anhydride Copolymer

Maleic anhydride copolymers that are suitable for use as polymeric binders in the preservative compositions of this invention may be formed with a variety of olefins. Of particular use are olefins of Structure I:

Structure I wherein R is $(CH_2)_x$—H were x=1-10, or phenyl.

The olefin is joined with maleic anhydride (Structure II) to form an olefin/maleic anhydride copolymer, a repeat unit of which is shown in Structure III:

Structure II

Structure III wherein R is $(CH_2)_x$—H; x=1-10, or phenyl; and n=about 10 to about 800.

Particularly suitable are copolymers where n=10 to about 400.

Octene/maleic anhydride and styrene/maleic anhydride are particularly suitable types of copolymers of the instant invention. Mixtures of different types of olefin/maleic anhydride copolymers, such as a mixture of octene/maleic anhydride copolymer and styrene/maleic anhydride copolymer may also be used. The synthesis of olefin/maleic anhydride copolymers is well known from sources such as U.S. Pat. Nos. 3,706,704 and 3,404,135.

Olefin/maleic anhydride copolymers of 2,000 and greater in molecular weight are suitable for use in this invention, and are generally between about 10,000 and about 50,000 in molecular weight. Copolymers of up to about 1,000,000 molecular weight may be used in the compositions of this invention, but if it is desired to provide a concentrated master batch of a preservative solution that is to be diluted prior to use, copolymers with greater than about 80,000 molecular weight are extremely viscous and are therefore difficult to use. Therefore, preferred in this invention are olefin/maleic anhydride copolymers with molecular weight ranging between 2,000 and about 80,000. More preferred are copolymers with molecular weights ranging between 2,000 and about 40,000.

A preferred process for the synthesis of styrene/maleic anhydride copolymers, which results in copolymers of molecular weight ranging between 20,000 and 100,000, makes use of a combination of toluene and isopropyl alcohol as both a solvent and as a chain transfer agent. Using this combination, rather than isopropyl alcohol alone, reduces the percent of mono isopropyl maleate ester formed during the polymerization from about 20% to about 1%. In addition, the molecular weight of the copolymer product is increased from about 18,000 when using isopropyl alcohol alone, to over 20,000 when using a toluene:isopropanol ratio of 1:1. Molecular weights of over 90,000 may be achieved using a ratio of 76:4. Olefin/maleic anhydride copolymers are also available commercially.

Preservative Metal Component

The fungitoxic metals copper and zinc, in ionic state, e.g. copper ion, may be combined with a hydrolyzed olefin/maleic anhydride copolymer in order to provide a preservative composition according to this invention. Any soluble copper salt may be a source of copper ions, for example Cu(II) salts may include copper sulfate, copper sulfate pentahydrate, cupric chloride, cupric acetate, and copper carbonate. Particularly useful as the copper salt is copper sulfate pentahydrate. Any soluble zinc salt may be a source of zinc ions, for example Zn(II) salts may include zinc sulfate, zinc chloride, zinc acetate, zinc nitrate, and zinc carbonate. Particularly useful as the zinc salt is zinc acetate. Mixtures of copper ion sources and zinc ion sources may be used in the compositions of this invention as well. Sources of copper ions and zinc ions, as described above, are available commercially.

Hydrolyzed Olefin/Maleic Anhydride Copolymer and Copper and/or Zinc Ion Solutions In the present invention, a solution comprising copper and/or zinc ions and at least one type of hydrolyzed olefin/maleic anhydride copolymer is made where the complexes of these components are sufficiently well dissolved such that the contents of the solution can be imbibed into a cellulosic material such as wood. Hydrolyzed olefin/maleic anhydride copolymer—copper/zinc complexes are typically insoluble in water. However, this type of complex is found to be soluble in a solvent system such as an ammoniacal solution.

The olefin/maleic anhydride copolymer is hydrolyzed to form negatively charged carboxylate anions that can complex with copper and zinc ions. For example, hydrolyzing with aqueous NaOH and complexing the resulting hydrolyzed olefin/maleic anhydride copolymer with copper is shown in Diagram IV.

Diagram IV

Hydrolysis to form carboxylic acid, maleic acid, derivatives in water in the presence of NaOH is described further in WO 97/15382.

A copper and/or zinc ion and hydrolyzed olefin/maleic anhydride copolymer solution is typically prepared by combining a solution of a copper and/or zinc salt and a solution of hydrolyzed olefin/maleic anhydride copolymer salt. Ammonium hydroxide may be added following the mixing of solutions of copper and/or zinc salt and hydrolyzed olefin/maleic anhydride copolymer salt, which then requires dissolving the formed precipitate. Alternatively, ammonium hydroxide may be included as a component in one or both of these solutions. Preferably the copper and/or zinc salt is prepared in an ammoniacal solution which is then combined with a hydrolyzed olefin/maleic anhydride copolymer salt solution. Ammonia is present in sufficient amount to maintain solubility of the copper and/or zinc and hydrolyzed olefin/maleic anhydride copolymer complex. Typically the ammonia is about 0.5% to 3% by weight in the final solution. Preferred is a 1.4% ammoniacal water solution. Ethanolamine may also be used at about 0.5% to 3% by weight. Additionally, combinations of ethanolamine and ammonia may be used. Although use of ammonia is preferred, other solvents or co-solvents that form a solution with water, that solubilize the complex as readily as ammonia, and also evaporate as readily as ammonia from the cellulosic material after treatment, may also be used in addition to or in place of ammonia or ethanol amine in the solvent system in which the complex is solubilized.

In general, solubility of the complex is determined by visual observation, and a complex is considered to be solbilized when a sufficient amount of the complex is dissolved in the solution to permit a desired amount of the complex to be adsorbed on and/or absorbed in the cellulosic material when the treatment thereof occurs.

The various components are used in the preservative compositions of this invention in amounts effective to provide a desired level of protection in view of the service conditions (including the nature of the target material, the contemplated end use, and the geographic location) that the cellulosic material to be treated will experience. The copper and/or zinc ions are typically used at a concentration in the treatment solution in the range of about 500 ppm to about 11,000 ppm. Marine use generally requires the higher concentrations, up to about 11,000 ppm while land use may involve concentrations between about 500 and 6,000 ppm. One method of determining the content of preservative components in a treated cellulosic material is to burn the material and analyze the ash for its content of the components that have been used to treat the material. A composition hereof may be made by mixing the components in any suitable device, such as a blender or rotating mixer.

Though the preservative compositions of this invention that are used in treating cellulosic materials are largely if not completely dissolved in solutions such as ammoniacal solutions, a more concentrated master batch may be made that is readily transported for commercial purposes, and then diluted prior to use. Such a concentrated master batch may be a slurry, containing partially precipitated hydrolyzed olefin/maleic anhydride copolymer and copper and/or zinc complexes. The slurry is prepared for use in treatment by increasing the volume of solution by the addition of one or more solvents or co-solvents, for example to a final concentration where ammonia is used in the solvent system and an approximately 1.4 wt % ammoniacal water solution is obtained.

A dry powder of copper and/or zinc ions and hydrolyzed olefin/maleic anhydride copolymer complex may also be provided to prepare a preservative solution for cellulosic material. This powder is prepared by combining solutions of copper and/or zinc salt and hydrolyzed olefin/maleic anhydride copolymer salt in the absence of ammonium hydroxide. A precipitate forms which may be collected from the remaining solution by standard methods such as centrifugation, filtering and spray drying. In addition the precipitate may be dried such as in a heated oven. This precipitate containing copper and/or zinc and hydrolyzed olefin/maleic anhydride copolymer complexes is soluble in ammoniacal solution for preparation of a preservative composition of this invention.

Features of Copper and/or Zinc and Hydrolyzed Olefin/Maleic Anhydride Copolymer Complex in Ammoniacal Solution as Preservative Compositions The solubility properties of the hydrolyzed olefin/maleic anhydride copolymer and copper and/or zinc complexes provide specific attributes valuable in a preservative composition for cellulosic materials. These complexes are insoluble in water but are typically well dissolved, if not completely soluble, in a solvent system such as an ammoniacal solution. When the complex is well dissolved in the solution, deep penetration of the preservative solution into a cellulosic material such as wood, well past the surface wood, is obtained. Following penetration, a solvent or co-solvent such as ammonia readily evaporates from the wood, leaving the antifungal copper and/or zinc complexed with the hydrolyzed olefin/maleic anhydride copolymer in the aqueous wood environment where it becomes precipitated and binds tenaciously to cellulose. The hydrolyzed olefin/maleic anhydride copolymer acts as a binding agent to retain the metal in the wood for long-term preservation. Thus there is little leaching of metal from the treated wood.

Preservative Composition and Additional Components

Though hydrolyzed olefin/maleic anhydride copolymers of 80,000 molecular weight may be used in preservative compositions of the instant invention, at this size an ammoniacal solution of copper and/or zinc and hydrolyzed olefin/maleic anhydride copolymer complexes is extremely viscous at a concentration that is convenient for shipping, to be diluted for use in wood treatment. Preferred for use in a preservative composition are hydrolyzed olefin/maleic anhydride copolymers ranging in size up to about 40,000 molecular weight, which provide adequately concentrated aqueous ammoniacal solutions that are convenient for shipping and are easily manipulated during dilution.

Preservative compositions of this invention may include antifungal and/or termiticidal components in addition to those discussed above, singly or in combinations. Examples include without limitation tungstate and/or molybdate ions as described in U.S. Provisional Application No. 60/755,213; ibuprofen as described in U.S. Provisional Application No. 60/755,214; and tropolones as described in U.S. Provisional Application No. 60/755,242; each of the above provisional applications being incorporated in its entirety as a part hereof for all purposes.

Molybdate and/or tungstate ions used as additional components in preservative solutions of this invention may be obtained from any soluble source of molybdate or tungstate, such as potassium molybdate, ammonium molybdate, sodium molybdate dihydrate, molybdenum oxide, molybdic acid, potassium tungstate, ammonium tungstate, sodium tungstate dihydrate, tungsten oxide, tungstic acid. Additional compounds that may be used as sources of tungstate or molybdate ions include compounds such as silicotungstates, phosphotungstates, borotungstates, silicomolybdates, phosphomolybdates and boromolybdates.

Molybdate and/or tungstate ions form complexes with copper and/or zinc ions that are insoluble in water, but that have substantial if not complete solubility in a solvent system such as an ammoniacal solution. These components penetrate a cellulosic material such as wood when dissolved in solution, and are retained in the wood after loss of the ammonia. When molybdate and/or tungstate ions are used as additional preservative components in a composition having complexes of copper and/or zinc, copper and/or zinc is added in sufficient amount to form complexes with both the ibuprofen component and the molybdate and/or tungstate component. Suitable amounts of molybdate and/or tungstate ions range from about 10 to about 6,000 ppm depending on factors related to the use to be made of the cellulosic material, as discussed above. Particularly suitable is a concentration between about 200 and about 1,700 ppm.

In a further embodiment, ibuprofen may be incorporated as an additional component of the compositions of this invention in view of its brown-rot fungicidal activity and termiticidal activity. Ibuprofen may be supplied as ibuprofen or sodium ibuprofenate. These compounds are soluble in methanol and ethanol but relatively insoluble in water. Ibuprofen forms a complex with copper and/or zinc that is insoluble in water, but has solubility in an ammoniacal solution that is similar to the solubility of the tropolone—copper and/or zinc complex described above. The complex formed by ibuprofen also penetrates a cellulosic material deeply when dissolved in the solution, and is retained in the wood after loss of a solvent or co-solvent such as ammonia. When ibuprofen is present as an additional component in a composition of this invention, copper and/or zinc ions are added in sufficient amount such that it/they form complexes with both the tropolone and the ibuprofen.

Ibuprofen or ibuprofenate may be included in a composition hereof in an amount in the range of from about 100 to about 1,000 ppm depending on the service conditions (including the nature of the target material, the contemplated end use, and the geographic location) that the cellulosic material to be treated will experience. Particularly suitable is a concentration of ibuprofen or ibuprofenate in the composition of between about 200 and about 700 ppm.

The term "tropolone" is commonly used to refer to tropolone itself (2-hydroxycyclohepta-2,4,6-trienone) and compounds that are derivatives of tropolone and have similar properties, such as the natural compounds beta-thujaplicin (also known as hinokitiol), gamma-thujaplicin, and beta-dolabrin. Any of these tropolones having antifungal and/or termiticidal activity may be used as additional components in the preservative compositions of this invention. These compounds are soluble in methanol and ethanol but relatively insoluble in water.

Tropolones also form complexes with copper and/or zinc ions that are insoluble in water but that have substantial if not complete solubility in a solvent system such as an ammoniacal solution. This component penetrates a cellulosic material such as wood when dissolved in solution, and is retained in the wood after loss of a solvent such as ammonia. When a tropolone is used as an additional preservative component in a composition containing copper and/or zinc ions, copper and/or zinc is added in an amount sufficient to form a complex with both the ibuprofen component and the tropolone component. Suitable amounts of tropolone for use in a composition hereof range from about 100 to about 1,000 ppm depending on factors related to the use to be made of the cellulosic material, as discussed above. Particularly suitable is a concentration between about 200 and about 700 ppm.

Preservative Treatment

The compositions of this invention, containing hydrolyzed olefin/maleic anhydride copolymer complexes with copper and/or zinc, and optionally containing additional antifungal and/or termiticidal compounds, may be applied by dipping, brushing, spraying, soaking, draw-coating, rolling, pressure-treating or other known methods. The preservative compositions may be applied to any cellulosic material, including for example wood, lumbar, plywood, oriented strand board, cellulose, hemicellulose, lignin, cotton, and paper. Particularly efficacious is imbibing into wood under the standard pressure treatment process for waterborne preservative systems. A vacuum may be applied before and/or after application of the wood preservative. Removal of air from the wood under vacuum, then breaking the vacuum in the presence of preservative solution, enhances penetration of the solution into the wood.

A particularly useful treatment process for wood is as follows: Wood, either dry or fresh cut and green is placed in a chamber that is then sealed and evacuated in a regulated cycle which is determined by the species of wood. Generally, for Southern Yellow Pine (SYP) wood, the period of evacuation is about 30 minutes, while the pressure within the sealed chamber is brought to a level of about two inches of mercury or less. The pressure in the chamber can vary from 0.01 to 0.5 atm. The purpose of this step is to remove air, water and volatiles from the wood. The aqueous compositions of the invention then are introduced into the closed chamber in an amount sufficient to immerse the wood completely without breaking the vacuum to the air. Pressurization of the vessel is then initiated and the pressure maintained at a desired level by a diaphragm or other pump for a given period of time. Initially, the pressure within the vessel will decrease as the aqueous composition within the container penetrates into the wood. The pressure can be raised to maintain a desirable level throughout the penetration period of treatment. Stabilization of the pressure within the vessel is an indication that there is no further penetration of the liquid into the wood. At this point, the pressure can be released, the wood allowed to equilibrate with the solution at atmospheric pressure, the vessel drained, and the wood removed. In this process, the pressures used can be as high as 300 psig, and are generally from about 50 to 250 psig.

Articles Incorporating Preservative Compositions

Articles of this invention are those having been treated with a preservative composition described herein. Following treatment of articles such as those made from or incorporating wood, lumber, plywood, oriented strand board, paper, cellulose, cotton, lignin, and hemicellulose, the ammonia in an ammoniacal solution of the preservative composition will dissipate. The articles retain the copper and/or zinc and hydrolyzed olefin/maleic anhydride copolymer. Additional antifungal and/or termiticidal components, if included in the preservative composition used for treatment, are retained in and/or on the treated articles as well.

Additional components for optional use in a composition of this invention may include tungstate and/or molybdate ions, ibuprofen, a tropolone, and mixtures of these. Particularly useful are articles containing copper and/or zinc and hydrolyzed olefin/maleic anhydride copolymer with molecular weight of at least 2,000 and at least one component selected from tungstate and/or molybdate ions, ibuprofen, a tropolone, and mixtures of these.

The process of this invention for treating cellulosic material also includes a step of incorporating the cellulosic material, or a treated article containing the cellulosic material, such as wood, into a structure such as a house, cabin, shed, burial vault or container, or marine facility, or into a consumable device such as a piece of outdoor furniture, or a truss, wall panel, pier, sill, or piece of decking for a building.

EXAMPLES

The present invention is further illustrated in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

The meaning of abbreviations is as follows: "sec" means second(s), "ml" means milliliter(s), "L" means liter(s), "g" means gram(s), "mmol" means millimole(s), "mtorr" means millitorr(s), "hr" means hour(s), "min" means minute(s), "mm" means millimeter(s), "cm" means centimeter(s), "nm" means nanometer(s), "Mw" means weight average molecular weight, "Mn" means number average molecular weight, "mw" means molecular weight, "XRF" stands for X-ray fluorescence spectroscopy, "RH" is relative humidity, "MHz" means megahertz, "NMR" means nuclear magnetic resonance, "IR" means infrared, "ICP" means ion coupled plasma, "LC/MS means liquid chromatography/mass spectroscopy, and "S/S" means stainless steel. "SD" is standard deviation, "SMA" is styrene/maleic anhydride copolymer, "SMA-NOH" is styrene/N-hydroxymaleamic acid copolymer, "OMA" is octene/maleic anhydride copolymer.

"SYP" is "southern yellow pine", an acronym for closely related pine species that includes *Pinus caribaea* Morelet, *Pinus elliottii* Englelm., *Pinus palustris* P. Mill., *Pinus rigida* P. Mill., and *Pinus taeda* L. "AWPA" is the American Wood-Preserver's Association. AWPA standards are published in. the "AWPA Book of Standards", AWPA, P.O. Box 5690, Granbury, Tex. 76049. The protocol for preservation of SYP stakes is based on AWPA Standard, Method E7-01, Sec. 4, 5, 6, and 7 and E11-97. According to AWPA Standard E7-01, the stakes are graded visually according to the following criterion for fungal decay and insect attack as follows:

Decay Grades

| Grade No. | Description of Condition |
| --- | --- |
| 10 | Sound. |
| 9.5 | Suspicion of decay permitted |
| 9 | Trace decay to 3% of cross section |
| 8 | Decay from 3 to 10% of cross section |
| 7 | Decay from 10 to 30% of cross section |
| 6 | Decay from 30 to 50% of cross section |
| 4 | Decay from 50 to 75% of cross section |
| 0 | Failure |

Termite Grades

| Grade No. | Description of Condition |
| --- | --- |
| 10 | Sound. |
| 9.5 | 1 to 2 small nibbles permitted |
| 9 | Slight evidence of feeding to 3% of cross section |
| 8 | Attack from 3 to 10% of cross section |
| 7 | Attack from 10 to 30% of cross section |
| 6 | Attack from 30 to 50% of cross section |
| 4 | Attack from 50 to 75% of cross section |
| 0 | Failure |

The termite grades and decay grades are used to report insect damage and wood decay, respectively, in the tables below. "Gross retention" refers to the amount of treatment liquid remaining in the wood immediately after imbibition. "Retention" refers to the amount of preservative remaining in the wood after the imbibing liquid has been removed from the wood by drying. The amount can be expressed as ppm or as a weight. A "witness stake" or "witness sample" is a whole stake, or a portion of a treated stake, that will be retained as a sample for future analysis.

General Methods

All reactions and manipulations were carried out in a standard laboratory fume hood open to atmosphere. Deionized water was used where water is called for in the subsequent procedures. Sorbitol, AIBN, acrylonitrile, lithium hydroxide monohydrate, hydroxylamine hydrochloride, copper sulfate pentahydrate, and Chromazurol S [1667-99-8] were obtained from Sigma-Aldrich Chemical (Milwaukee, Wis.) and used as received. Concentrated ammonium hydroxide and glacial acetic acid were obtained from EM Science (Gibbstown, N.J.) and used as received. Cyanoethylated sucrose [18307-13-7] and copper acetate monohydrate were obtained from Acros Organics (Geel, Belgium) and used as received. Sucrose was obtained from Pathmark Supermarket (Wilmington, Del.) and used as received.

Elemental analyses were performed by Micro-Analytical Inc, Wilmington, Del. Pressure treatment of southern yellow pine wood was performed in a high-pressure lab using stainless steel pressure vessels following the AWPA standard process (AWPA P5-01). XRF analysis was performed on an Axios Wavelength Dispersive X-ray Fluorescence Spectrometer manufactured by Panalytical Inc., Eindhoven, Netherlands.

Chromazurol-S Test for Presence of Copper

Treated wood was tested for the presence of copper with Chromazurol S using the method described by AWPA A3-00 Sec. 2. A 0.167% w/w Chromazurol S in 1.67% w/w aqueous sodium acetate solution was sprayed onto a freshly cut treated wood surface. A change from the yellow solution color to a dark blue color in the sprayed area indicates that a minimum of 25 ppm copper is present. Stakes 965 mm (38") long were cut to 457 mm (18") from each end and the remaining 50.8 mm (2") piece (witness piece) in the middle was treated on the freshly cut surface with a solution of Chromazurol-S. When the freshly cut surface turns dark blue on exposure to the solution, it is an indication of complete penetration of the wood by the wood preservative treatment solution.

All wood was cut using inch measurements. The wood was cut as accurately as practicable, given that wood will change dimensions with moisture content; the cutting error is estimated to be within one mm in any dimension. Conversions to metric are provided.

Fahlstrom stake: 0.156"×1.5"×10" (4 mm×38 mm×254 mm)
Pre-Decay stakes: ¾"×¾"×38" (19 mm×19 mm×1154 mm)
Decay stake: ¾"×¾"×18" (19 mm×19 mm×450 mm)
Depletion stake: 1.5"×1.5"×18" (38 mm×38 mm×450 mm)
Blocks: ¾"×¾"×¾" (19 mm×19 mm×19 mm)

Example 1

Ammoniacal Solution of Hydrolyzed Octene/Maleic Anhydride Copolymer Copper Complex as Preservative A1) Preparation of Hydrolyzed Octene/Maleic Anhydride Copolymer Copper Complex in Ammoniacal Solution A 1:1 co-polymer of octene and maleic anhydride monosodium salt was prepared as described in U.S. Pat. No. 3,706,704 and U.S. Pat. No. 3,404,135. The Mw of the octane/maleic anhydride, which is the precursor of hydrolyzed 1:1 octene/maleic anhydride copolymer monosodium salt, was determined by size exclusion chromatography using a multi-angle light scattering detector. The Mw of the octene/maleic anhydride copolymer was determined to be 8595+/−50. The size exclusion chromatography was performed on a Waters 2690 Liquid Chromatograph (Waters Corp., Milford, Mass.) and the detector was a Wyatt Technology Light Scattering Detector (Wyatt Technology, Santa Barbara, Calif.). The resulting co-polymer was hydrolyzed with aqueous sodium hydroxide solution and brought to a 27.8% w/w solution in water. Then 42.13 g of the hydrolyzed 1:1 octene/maleic anhydride co-polymer monosodium salt solution was placed in a 1 L bottle, and 300 g of water and 6 g of ammonium hydroxide were added. The mixture was mixed well. Separately, 5.835 g of $CuSO_4.5H_2O$ was dissolved in 70 ml of water. All of this copper solution was added to the hydrolyzed 1:1 octene/maleic anhydride co-polymer monosodium salt solution, and a precipitate was observed which indicated insolubility of the copper complexed with the octane/maleic anhydride copolymer. An additional 9 g of ammonium hydroxide was added to the copper and hydrolyzed octane/maleic anhydride co-polymer mixture, and the precipitate immediately dissolved. The solution was brought to 1L with water to obtain a solution containing 1485 ppm of Cu. The mixture was allowed to stand at room temp for 1 hour. The copper complexed with octane/maleic anhydride co-polymer remained in solution, demonstrating that hydrolyzed octane/maleic anhydride co-polymer of molecular weight 8595 +/−50 and complexed with copper is soluble in ammoniacal solution.

A2) Alternative Preparation of Ammoniacal Solution of Hydrolyzed Octene/Maleic Anhydride Copolymer and Copper Complex Preservative Solution 300 g of water was slowly added to 47.8 g of sulfuric acid in a beaker. 37.2 g of CuO was slowly added to the sulfuric acid in portions, during 15 min with stirring. The reaction was exothermic with the temperature rising from 45° C. to 60° C. All of the CuO was soluble in 45 minutes. To avoid the insolubility problem associated with directly combining the copper solution and octene/maleic anhydride co-polymer complex, an ammoniacal solution of the CuO was prepared prior to addition of the octene/maleic anhydride co-polymer. 120 g of concentrated $NH_4OH$ was added to the CuO and sulfuric acid solution, and the color turned a deep blue. To this solution, 469.5 g of a 27.1% w/w solution of hydrolyzed 1:1 octene/maleic anhydride co-polymer monosodium salt solution was added, followed by addition of 80 g of $NH_4OH$ and 145 g of water. To the resulting solution, a 28% w/w concentrated ammonium hydroxide solution was added for a final concentration of 1.4% w/w ammonia in water and a final weight of 20 Kg. The above procedure was repeated three times producing a total of 3 separate 20 Kg solutions, each having a concentration of 1485 ppm copper.

To prepare 20 Kg of a wood treatment solution containing 742 ppm copper, 10 L of the 1485 ppm copper solution above was diluted with 1.4% w/w ammonia water to give a final weight of 20 Kg. To prepare 20 Kg of a wood treatment solution containing 371 ppm copper, 10 Kg of the 742 ppm copper solution was diluted with 1.4% w/w ammonia water to give a final weight of 20 Kg.

B) Penetration of Ammoniacal Solution of Hydrolyzed Octene/Maleic Anhydride Co-polymer and Copper Complex in Wood Blocks The ammoniacal solution of hydrolyzed octene/maleic anhydride co-polymer and copper complex prepared in Example 1 A1 was imbibed into wood using a wood impregnation system similar to that described by the American Wood Preservers Association (AWPA) as AWPA Standard, Method E11-97. Standard laboratory glassware and a vacuum pump were used to imbibe 32 pre-weighed Southern Yellow Pine (SYP) wood blocks measuring ¾"×¾"×¾" (19 mm×19 mm×19 mm). The blocks were free of knots, resin and sap pockets, had no visible sign of infection by mold, stain, and wood destroying fungi, had no cracks, had a ring count of 6-10 rings per inch, and contained at least 50% summer wood. The blocks were pre-conditioned for 21 days in a humidity chamber set at 23° C.+/−0.5° C. and relative humidity of 50% +/−2%. Under these conditions the blocks achieved equilibrium moisture content of 9-10%, which was determined by using a Moisture Meter, Model PM6304 from the Control Company (Friendswood, Tex). An imbibing vessel was prepared using a glass flask measuring 10.16 cm in diam.×30.48 cm long having three openings, two of which were standard taper ground glass 29/26 joints and one central joint having a standard taper ground glass 102/75 ball joint. An addition funnel was placed on one of the 29/26 joints and filled with the treatment solution. The wood cubes were placed in the imbibing vessel in a Nylon bag that was weighted with stainless steel nuts to prevent floating and the imbibing vessel was evacuated for 30 min. The vacuum was broken by introduction of 800 ml of imbibing solution. This amount of solution was sufficient to cover the blocks. Thirty-two blocks were imbibed with the hydrolyzed octane/maleic anhydride co-polymer monosodium salt/copper complex solution prepared in A1. The blocks were imbibed under atmospheric pressure for 30 minutes. The blocks were gently wiped with a towel to remove any surface solution and were then immediately weighed while wet to ensure that the wood was penetrated by the imbibing solution. Table 1, including gross retention calculations, shows that the blocks gained weight which indicated that the ammoniacal solution of hydrolyzed octene/maleic anhydride co-polymer and copper complex was successfully imbibed into wood.

TABLE 1

Gross retention in SYP blocks treated with ammoniacal solution of hydrolyzed octane/maleic anhydride co-polymer complexed with copper.

| ID# | dry wt (g) | wet wt (g) | Gross Retention (g) | |
|---|---|---|---|---|
| E2000111.00173A1 | 3.7498 | 8.7404 | 4.9906 | * |
| E2000111.00173A2 | 3.7508 | 8.8462 | 5.0954 | * |
| E2000111.00173A3 | 3.7070 | 8.8892 | 5.1822 | |
| E2000111.00173A4 | 3.8650 | 8.7248 | 4.8598 | |
| E2000111.00173A5 | 3.7513 | 8.7256 | 4.9743 | * |
| E2000111.00173A6 | 3.7857 | 8.6350 | 4.8493 | |
| E2000111.00173A7 | 3.7274 | 8.6582 | 4.9308 | |
| E2000111.00173A8 | 3.8020 | 8.8395 | 5.0375 | * |
| E2000111.00173A9 | 3.7122 | 8.9103 | 5.1981 | |
| E2000111.00173A10 | 3.7268 | 8.8861 | 5.1593 | |
| E2000111.00173A11 | 3.8081 | 8.6499 | 4.8418 | |
| E2000111.00173A12 | 3.7453 | 8.9203 | 5.1750 | |
| E2000111.00173A13 | 3.8372 | 8.7574 | 4.9202 | * |
| E2000111.00173A14 | 3.7170 | 8.8388 | 5.1218 | |
| E2000111.00173A15 | 3.7493 | 8.6163 | 4.8670 | |
| E2000111.00173A16 | 3.7076 | 8.7419 | 5.0343 | * |
| E2000111.00173A17 | 3.7868 | 8.9227 | 5.1359 | * |
| E2000111.00173A18 | 3.8094 | 6.7546 | 2.9452 | |
| E2000111.00173A19 | 3.8578 | 8.9584 | 5.1006 | * |
| E2000111.00173A20 | 3.7164 | 8.4940 | 4.7776 | |
| E2000111.00173A21 | 3.8533 | 8.8678 | 5.0145 | * |
| E2000111.00173A22 | 3.7905 | 8.7730 | 4.9825 | * |
| E2000111.00173A23 | 3.7026 | 8.5858 | 4.8832 | |
| E2000111.00173A24 | 3.7610 | 8.6763 | 4.9153 | |
| E2000111.00173A25 | 3.8217 | 8.9593 | 5.1376 | |
| E2000111.00173A26 | 3.8397 | 8.8805 | 5.0408 | * |
| E2000111.00173A27 | 3.7743 | 8.8478 | 5.0735 | * |
| E2000111.00173A28 | 3.8385 | 8.9147 | 5.0762 | * |
| E2000111.00173A29 | 3.7844 | 9.0343 | 5.2499 | |
| E2000111.00173A30 | 3.7624 | 8.6059 | 4.8435 | |
| E2000111.00173A31 | 3.7489 | 8.6975 | 4.9486 | |
| E2000111.00173A32 | 3.8497 | 8.7338 | 4.8841 | |

* marks blocks having a gross retention falling within +/−5% of the group average From the 32 SYP blocks treated as above, 6 blocks having a gross retention falling within +/−5% of the group average were chosen. These blocks were chosen from those marked with an asterisk in Column 5 of Table 1 and are listed in Table 2. The blocks were dried at room temperature for 2 weeks, and were again conditioned for 21 days in a humidity chamber set at 23° C.+/−0.5° C. and relative humidity of 50%+/−2%. Weights of the conditioned blocks (wt before leaching) were then recorded in Table 2.

TABLE 2

Weights of SYP wood blocks at different stages of treatment.

| ID# | dry (wt) (g) | wet wt (g) | Gross retention (g) | Wt before leach (g) | Wt after leach test (g) |
|---|---|---|---|---|---|
| E2000111.00173A2 | 3.7508 | 8.8462 | 5.0954 | 3.8108 | 3.6646 |
| E2000111.00173A8 | 3.8020 | 8.8395 | 5.0375 | 3.8608 | 3.7158 |
| E2000111.00173A13 | 3.8372 | 8.7574 | 4.9202 | 3.8829 | 3.7381 |

TABLE 2-continued

Weights of SYP wood blocks at different stages of treatment.

| ID# | dry (wt) (g) | wet wt (g) | Gross retention (g) | Wt before leach (g) | Wt after leach test (g) |
|---|---|---|---|---|---|
| E2000111.00173A17 | 3.7868 | 8.9227 | 5.1359 | 3.8489 | 3.7069 |
| E2000111.00173A22 | 3.7905 | 8.7730 | 4.9825 | 3.8343 | 3.6923 |
| E2000111.00173A27 | 3.7743 | 8.8478 | 5.0735 | 3.8389 | 3.6936 |
| Totals | 22.7416 | | 30.2450 | 23.0766 | 22.2113 |

The amount of active ingredient contained in the six wood blocks was calculated based on the weight of treatment solution contained and the weight fraction of active ingredient in the treatment solution. The total uptake of imbibing solution for the six blocks was 30.2450 g (see Table 2). The concentration of copper in the imbibing solution was 1485 ppm. Therefore, the total amount of copper in the six blocks was (30.2450 g) (1485 ppm)/1,000,000=0.04491 g copper.

C) Retention of Ammoniacal Solution of Hydrolyzed Octene/Maleic Anhydride Copolymer and Copper Complex in Wood Blocks The 6 selected blocks in Example 1B were reintroduced into the imbibing vessel, which was evacuated for 30 minutes, and 150 ml of deionized water was added to break the vacuum. The submerged blocks were imbibed with water for 30 minutes at atmospheric pressure. The remainder of the water imbibing solution was transferred to a measuring cylinder and the volume brought to 300 ml with deionized water. The blocks and water were transferred to a jar and the jar was covered. Six blocks were imbibed separately with 150 ml of deionized water to serve as a control; these blocks were removed and placed in a leaching jar. The excess water was placed in a volumetric cylinder and made up to a total of 300 ml with DI water and the control blocks were then leached as per the treated blocks. The leaching jars were agitated at 23° C.+/−0.5° C. at 100 oscillations/min on an Innova 2300 Platform Shaker table (New Brunswick Scientific Co., Inc., Edison, N.J.). The water from each jar was collected as a leachate solution and replaced with 300 ml of fresh deionized water at the following hourly intervals: 6, 24, 48, 96, 144, 192, 240, 288, 336, and 384 hours. The individual leachate solutions were analyzed for copper content by the following procedure: The leachate sample was evaporated to dryness in a jar using an oven set at 95° C. Then 1 g of sulfamic acid and 50 ml of deionized water was added and the jar was heated to 100° C. for 30 minutes. The jar was cooled to room temperature and then 6 g of aluminum sulfate octadecahydrate was added. A 15% sodium carbonate solution was used to bring the pH to neutral, followed by addition of about one to three ml of glacial acetic acid to bring the pH to approximately 4. Then 7 g of NaI was added to the room temperature solution. The solution was titrated with 0.00919 M sodium thiosulfate solution. When the solution appeared to be straw-colored, a freshly prepared solution of 1 g of soluble starch in 100 ml of water and 1 g of potassium thiocyanate was added. The solution was then titrated with 0.00919 M sodium thiosulfate solution to the discharge of the blue starch/iodide color. The amount of copper present in each sample of leachate was calculated by the equation:

g Cu=(ml 0.00970 N sodium thiosulfate)(0.00970 equiv./1000 ml)(63.546 g Cu/equiv.).

From the titration of the leachate collected at each time given above, the total amount of copper remaining in the six blocks was computed as the difference between the amount determined by titration of the leach solution and the value for the previous time point (see Table 3).

TABLE 3

Leaching of copper from SYP wood blocks treated with ammoniacal solution of hydrolyzed octane/maleic anhydride co-polymer complexed with copper.

| Hours | Vol. 0.01N thiosulfate | g Cu in leachate | Calculated g Cu remaining in blocks |
|---|---|---|---|
| 0 | 0.00 | 0.00000 | 0.04491 |
| 6 | 1.20 | 0.00074 | 0.04417 |
| 24 | 0.46 | 0.00028 | 0.04389 |
| 48 | 0.19 | 0.00012 | 0.04377 |
| 96 | 0.10 | 0.00006 | 0.04371 |
| 144 | 0.10 | 0.00006 | 0.04365 |
| 192 | 0.05 | 0.00003 | 0.04362 |
| 240 | 0.05 | 0.00003 | 0.04359 |
| 288 | 0.05 | 0.00003 | 0.04356 |
| 336 | 0.00 | 0.00000 | 0.04356 |
| 384 | 0.00 | 0.00000 | 0.04356 |
| Totals | 2.2 | 0.00135 | — |

Six untreated control blocks were treated and leached as above and titrated with 0.00937 N thiosulfate to yield 0.000178 g of leachable copper background. This amount of copper was subtracted from the total amount of copper that was leached from the treated blocks (0.00135 g, Table 3) to give 0.001172 g of copper leached from the preservative. The amount of copper initially imbibed into the wood was 0.04491 g. Therefore only about 2.61%=[(0.001172/0.04491) (100)] of the copper leached out of the wood under these vigorous leaching conditions. This result shows that there is excellent retention of copper in the wood when it is complexed with hydrolyzed octane/maleic anhydride copolymer.

After leaching, the blocks were weighed. Block weights (wt after leach test) are given in Table 2 above. This data shows that the blocks weigh slightly after leaching.

D) Wood Preparation Treatment Procedure and Environmental Testing for Decay Stakes The following methods are based on AWPA Standard, Method E7-01, Sec. 4, 5, 6, and 7 and E11-97.

SYP boards, ⅝"×14"×8 ft (3.175 cm×35.56 cm×243.84 cm) and ⅝"×12"×8 ft (3.175 cm×30.48 cm×243.84 cm) were obtained from Delaware County Supply (Boothwin, Pa.). The boards were cut into pre-decay stakes of ¾"×¾"×38" (19 mm×19 mm×96.5 cm) in size (AWPA Standard, Method E7-01, Sec 4.2, with the exception that the boards were milled without equilibration). The stakes were segregated by visual inspection (AWPA Standard, Method E7-01, Sec. 4.1) and stakes having knots, cracks, resin and sap pockets, signs of infection by mold, stain, and wood destroying fungi were eliminated. The remaining stakes were sorted into groups by weight (AWPA Standard, Method E7-01, Sec. 5). The group of pre-decay stakes weighing between 200 g and 220 g was chosen for the imbibing experiment and placed in a controlled environment chamber at 23° C. and RH of 50% (Model 1-60LLVL Humidity Cabinet, Percival Scientific Inc., Boone, Iowa) for 21 days (AWPA Standard, Method E7-01, Sec. 4 and E11-97, Sec. 3). After equilibration in the environment chamber, each stake was equipped with two S/S identification tags and secured with 24.6 mm S/S nails. Each stake was then weighed (weights given in Table 4: Dry weight) and dimensioned and the results recorded.

Wood Preservation Treatment Procedure

Treatment was carried out in a stainless steel pressure vessel designed and fabricated at the DuPont Experimental Station (Wilmington, Del.). Pressure was supplied by a Diaphragm Pump (Model S216J10; Sprague Products Div. of Curtiss-Wright Flow Control Corp., Brecksville, Ohio). The pressure vessel was constructed from sched. 80 S/S pipe measuring 12.7 cm (5") diameter and was closed at each end with S/S flanges and caps. The length of the pipe varied depending on the length of the wood to be treated. Typically, a 40" (101.6 cm)=length was chosen for treating 38" wood specimens. Other lengths of pipe were added via flanges to extend the length of the pressure vessel to accommodate 8 ft (243.84 cm) specimens or shorter lengths of pipe were used to treat 10" (25.4 cm) specimens.

Ten labeled stakes were loaded into a stainless steel separation rack (to simulate sticking, which is physical separation of lumber by placing small pieces of wood between boards to separate them) as well as two witness stakes (total 12 stakes), and placed in the pressure vessel. The pressure vessel was sealed and a vacuum of 69.85 cm Hg gauge (13.5 psig) was applied for a period of 30 minutes. The vacuum was broken by introduction of the imbibing fluid to fill the pressure vessel and cover the wood. The imbibing fluid used was prepared in Example 1 A1 and contained 1485 ppm copper. Air pockets were removed by circulating imbibing fluid through the vessel, and pressure of 7.18 kilopascal gauge (150 psig) was applied with a diaphragm pump for a period of 30 minutes. The pressure was released and the stakes allowed to equilibrate in the imbibing solution for 15 minutes. The pressure vessel was drained and the treatment rack bearing the stakes was removed. The stakes were lightly wiped with a paper towel, weighed (weights given in Table 4: Wet weight), and placed on open racks in a ventilated enclosure to dry. The original dry weight subtracted from the wet weight for each block indicated the amount of uptake of treatment solution, as given in Table 4.

TABLE 4

Retention of Treatment Solution in SYP Pre-decay Stakes.

| Stake ID | Dry Wt. (g) | Wet Wt. (g) | Gross Retention (g) |
|---|---|---|---|
| W0727 | 217.76 | 460.21 | 242.45 |
| W0729 | 218.82 | 458.7 | 239.88 |
| W0731 | 209.56 | 456.32 | 246.76 |
| W0733 | 217.67 | 455.91 | 238.24 |
| W0735 | 208 | 458.72 | 250.72 |
| W0737 | 224.83 | 445.52 | 220.69 |
| W0739 | 213.13 | 454.8 | 241.67 |
| W0741 | 221.28 | 467.07 | 245.79 |
| W0743 | 219.88 | 455.35 | 235.47 |
| W0745 | 211.66 | 455.53 | 243.87 |

After 14 days the stakes were weighed, the results recorded, and returned to the humidity chamber. After a total of 21 days in the chamber, the stakes were weighed and the results recorded (AWPA Standard, Method E7-01, Sec. 6). The similarity in weights at 14 and 21 days indicated that the interior moisture level had reached a constant value.

The 10 labeled pre-decay stakes were cut to 45.7 cm (18") lengths (decay stake length), cutting from each end and leaving a 5.1 cm (2") witness section from the center of the stake. All witness sections were tested for copper penetration using the Chromazurol S test described in the General Methods. All witness sections tested turned dark blue indicating complete penetration of the wood by the wood preservative treatment solution.

Each 45.7 cm (18") decay stake was weighed, dimensioned and the results recorded. The group of 10 stakes from each half were bundled together and labeled for ground insertion at two separate test sites (Newwark Del. and Starke, Fla.). The bundles were stored in a cool area (AWPA Standard, Method E7-01, Sec. 7) until the stakes were installed in the ground. The treated stakes, along with untreated control stakes, were placed on the ground as per AWPA E7-01. The positioning of the stakes was randomized in the test sites as per AWPA E7-01. After 12 months the stakes were removed from the ground and visually graded for decay and termite attack according to AWPA protocol E7-01. Gradings for the stakes tested in Starke, Fla. are given in Table 5.

TABLE 5

Decay and insect damage data for stakes treated with ammoniacal solution of hydrolyzed octene/maleic anhydride copolymer copper complex tested in Starke, FL.

| Treatment | Stake ID | 12 mo grading/score | |
|---|---|---|---|
| | | decay | Insect damage |
| 1485 ppm Copper/hydrolyzed OMA | 728 | 10 | 10 |
| | 730 | 9.5 | 9 |
| | 732 | 10 | 10 |
| | 734 | 10 | 10 |
| | 736 | 10 | 10 |
| | 738 | 10 | 10 |
| | 740 | 10 | 10 |
| | 742 | 10 | 10 |
| | 744 | 8 | 10 |
| | 746 | 10 | 10 |
| | Avg | 9.75 | 9.9 |
| | SD | 0.60 | 0.3 |
| Untreated Controls | 1440 | 0 | 0 |
| | 1442 | 8 | 6 |
| | 1444 | 0 | 0 |
| | 1446 | 6 | 6 |
| | 1448 | 6 | 6 |
| | 1450 | 6 | 4 |
| | 1452 | 6 | 6 |
| | 1454 | 6 | 4 |
| | 1456 | 0 | 0 |
| | 1458 | 6 | 6 |
| | Avg | 4.4 | 3.8 |
| | SD | 2.94 | 2.6 |

Additional stakes were treated with 1:2 and 1:4 dilutions of the same treatment solution and tested at Starke, Fla. and Newark, Del. A summary of decay and insect attack results for stakes with undiluted and diluted treatments at two sites is given in Table 6.

TABLE 6

Averages of decay and insect damage data for stakes treated with different concentrations of ammoniacal solution of hydrolyzed octene/maleic anhydride copolymer copper complex tested in Newark, DE and Starke, FL.

| Location | Treatment: Conc. in ppm | Time (Months) | Avg. Decay | Avg. Insect damage |
|---|---|---|---|---|
| Starke, FL | Cu 1485/ hydrolyzed OMA | 12 | 9.75 | 9.9 |
| | Cu 743/ hydrolyzed OMA | 12 | 9.65 | 9.9 |
| | Cu 371/ hydrolyzed OMA | 12 | 8.7 | 8.9 |
| | Control | 12 | 4.4 | 3.8 |
| Newark, DE | Cu 1485/ hydrolyzed OMA | 12 | 10 | 10 |
| | Cu 743/ hydrolyzed OMA | 12 | 10 | 10 |
| | Cu 371 hydrolyzed/ OMA | 12 | 9.65 | 9.9 |
| | Control | 12 | 8.8 | 9.75 |

With damage to controls extensive, strong protection by all treatment solutions was observed at the Starke, Fla. site. There is little decay and insect damage at the Newark site in 12 months due to the colder climate and lesser amount of rainfall. It is expected that over longer periods of time, treated decay stakes at the Newark site will show less fungal attack and insect damage with respect to controls.

Example 2

Preparation of Hydrolyzed 1:1 Octene/Maleic Anhydride Co-Polymer Copper Salt as a Readily Solubilized Powder For shipping purposes it may be desirable to prepare the copper complex in powdered form to avoid shipping dilute aqueous solutions. A readily soluble powder was prepared as-follows.

A solution of 11.7 g of $CuSO_4.5H_2O$ in 40 g of water was prepared. To this solution was added a mixture of 1.87 g NaOH and 43.3 g of hydrolyzed 1:1 octene/maleic anhydride co-polymer monosodium salt as a 27.8% w/w solution in water. A precipitate formed. The slurry was filtered through Whatman No. 1 filter paper to isolate the precipitate. The precipitate was partially air-dried followed by further drying in a 90° C. oven for 2 hours to a final weight of 26.5 g. The solid contains 57% 1:1 octene/maleic anhydride co-polymer copper salt complex and 43% water. The precipitate was soluble in 1.4% ammonia water.

Example 3

Preparation of Styrene/Maleic Anhydride Copolymer (SMA)

The copolymerization of styrene and maleic anhydride using isopropyl alcohol as both a solvent and as a chain transfer agent to limit the molecular weight of the copolymer (SMA) is described in U.S. Pat. No. 3,404,135. However, we have found that about 20% of the maleic anhydride reacted to form mono isopropyl maleate ester during the polymerization. The Mn of the copolymer resulting from the use of isopropyl alcohol as a solvent was typically about 7200 and the Mw was about 17,000. When toluene was used as the solvent and chain transfer agent, no ester was formed but the reaction product was a sticky mass that was not easy to recover by filtration. The Mn of the copolymer resulting from the use of toluene as the reaction solvent was about 9,000 and the Mw was about 35,000. We have found that a combination of toluene and isopropyl alcohol serves as both a solvent for the monomers and a chain transfer agent to limit the molecular weight of the copolymer. The Mn of the copolymer was about 20,900 and the Mw was about 47,400. The amount of ester formed in the polymerization was about 1%. The reaction product, SMA, was a powder that was insoluble in the reaction solvent and was easy to collect by filtration.

Small Scale SMA Preparation

Into a 500 ml round bottomed flask equipped with mechanical stirrer, condenser, thermocouple well, mineral-oil filled nitrogen bubbler, and addition funnel was charged 71 g of toluene and 4 g of isopropyl alcohol. The solvent mixture was heated to 60° C. using an oil bath as a heat source. To the hot solvent was added 9.8 g of maleic anhydride. The mixture was stirred to dissolve the maleic anhydride and then warmed to 70° C. To this mixture was added a solution of 0.125 g of AIBN in 5 g of toluene. The flask was swept with nitrogen and then, during 2 minutes, 10.4 g of styrene was added dropwise through the addition funnel. After a few minutes, a white precipitate began to form. The reaction temperature was kept at 72° C. for 150 minutes and then raised to and held at 80° C. for 30 minutes. The reaction was then cooled to room temperature and the copolymer collected by filtration. The polymer powder was washed with 20 g of toluene and then air dried at 80° C. in an oven to give 19.3 g of a white, freely flowing powder. The Mw=54,400 and the Mn=23,200. The washings were evaporated to give an additional 0.4 g of mono isopropyl maleate ($^1$H NMR (THF-d$_8$): δ1.23 (d, CH3, 6H), 5.2 (m, CH, 1H), 6.2 (m, CH, 2H) ppm.

The process was repeated using toluene and acetic acid or different ratios of toluene and isopropanol, as well as different temperatures as given in Table 7. The Mn and Mw of the SMA product varied as shown in Table 7.

nels. The second funnel was charged with 1302.6 g of styrene. The apparatus was sealed and purged with nitrogen. The maleic anhydride solution was warmed to 60° C. and about one-third of the AIBN solution was added. Then about 150 ml of styrene was added to the flask from the funnel. There was about a 5 minute induction period during which oxygen was consumed. After a white precipitate began to form, indicating that the polymerization had begun, the remaining styrene was added in 150 ml portions during 60 minutes. The AIBN solution was added in thirds over 60 minutes. The addition of styrene and AIBN maintained the reaction temperature at about 70° C. to 80° C. without much additional heat from the mantel. After addition was complete, the reaction temperature was maintained at about 80° C. for an additional 2 hours by using the heating mantel. The white slurry of copolymer was then cooled to about room temperature, filtered, washed with warm toluene, and dried in a vacuum oven at 90° C. to obtain 2460 g (95.5% yield) of SMA and 40 g of mono isopropyl maleate. The Mw=40,400 and the Mn=18,600. The washings were evaporated to give 0.4 g of mono isopropyl maleate ($^1$H NMR (CDCl$_3$): δ1.32 (d, J=1.2, CH3, 6H), 5.15 (m, CH, 1H), 6.36 (m, CH, 2H) ppm.

Example 4

Ammoniacal Solution of Hydrolyzed 1:1 Poly(Styrene/Maleic Anhydride) Copolymer Copper Salt as Preservative A) Preparation of Hydrolyzed 1:1 Poly(Styrene/Maleic Anhydride) Copolymer Copper Salt in Ammoniacal Solution A solution of 37.44 g of NaOH and 100 g of water was added to 94.63 g of 1:1 styrene/maleic anhydride co-polymer. The mixture was stirred and warmed to 50° C. to dissolve and hydrolyze the polymer. The clear solution was allowed to cool to room temperature (25° C.). A solution of 116.85 g of CuSO$_4$.5H$_2$O was prepared in a mixture of 250 g of concentrated ammonium hydroxide and 500 g of water. The concentrated solution of the copper complex of hydrolyzed styrene/

TABLE 7

Effect of solvent on Mn and Mw of SMA

| Solvent System | Mn | Mw | Comments |
| --- | --- | --- | --- |
| toluene/acetic acid: 80:1 | 24,400 | 162,200 | reaction temperature not controlled |
| toluene/acetic acid: 80:1 | 28,700 | 90,000 | reaction temperature controlled to 80 C. |
| toluene/isopropanol: 76:4 | 28,200 | 95,800 | initial reaction temp 60, then 72 for 2.5 hours |
| toluene/isopropanol: 76:4 | 23,000 | 54,400 | initial reaction temp 50, then 72 for 2.5 hours and 80 C. for .5 hour |
| toluene/isopropanol: 25:55 | 11,900 | 25,900 | intial reaction temp 60, then 70 for 1 hour then reflux 1 hour |
| toluene/isopropanol: 40:40 | 2,920 | 22,100 | initial reaction temp 60 then 70 for 1 hour then 80 for 1 hour |
| toluene/isopropanol: 40:40 | 13,200 | 33,300 | initial reaction temp 60 then 70 for 2.5 hours |
| toluene/isopropanol: 40:40 | 4,810 | 26,500 | initial reaction temp 60 then 84 for 2 hours |
| toluene/isopropanol: 40:40 | 5,080 | 21,100 | intial reaction temp 60 then 84 for 2 hours |
| toluene/isopropanol: 40:40 | 10,900 | 26,400 | initial reaction temp 60 then 83 for 1 hour |
| toluene | 9,400 | 35,400 | exothermic reaction 100 to 110 |
| isopropanol | 7,230 | 17,700 | reflux I hour |
| tetrahydrofuran | 1,080 | 7,330 | reflux 3 hours |

Large Scale Preparation

An 18 L multi-necked flask was equipped with two dropping funnels, reflux condenser, heating mantel, mechanical stirrer, and nitrogen bubbler. The flask was charged with 9500 g (11 L) of toluene and 500 g (640 ml) of isopropanol. To this solution was added 1276 g of maleic anhydride powder. A solution of 15 g of AIBN dissolved in 500 g (578 ml) of toluene was prepared and placed in one of the dropping funmaleic anhydride copolymer was diluted with 1.4% ammonia solution to prepare 20 Kg of 1485 ppm Cu preservative solution.

B) Penetration of Ammoniacal Solution of Hydrolyzed Styrene/Maleic Anhydride Copolymer and Copper Complex in Wood Blocks The ammoniacal solution of hydrolyzed styrene/maleic anhydride co-polymer and copper complex prepared in Example 4A was imbibed into wood using a wood impregnation system similar to that described by the American Wood Preservers Association (AWPA) as AWPA Standard, Method E11-97 as described in Example 1B. Table 8, including gross retention calculations, shows that the blocks gained weight indicating that the ammoniacal solution of hydrolyzed styrene/maleic anhydride co-polymer and copper complex was successfully imbibed into the wood.

From the 32 SYP blocks treated as above, 6 blocks having a gross retention falling within +/−5% of the group average were chosen and are listed in Table 9. The blocks were treated and calculations made as described in Example 1B. A total of 29.7411 g of 1485 ppm copper imbibing solution was retained, or 0.04417 g copper was retained.

TABLE 9

Weights of SYP wood blocks at different stages of treatment.

| ID# | Wt. Dry (g) | Wt wet (g) | Diff (g) Gross retention | Wt before leach (g) | Wt after leach (g) | Diff (g) |
|---|---|---|---|---|---|---|
| E2000111.00172A7 | 4.0554 | 9.0485 | 4.9931 | 4.122 | 4.0064 | 0.1156 |
| E2000111.00172A8 | 4.0819 | 9.0566 | 4.9747 | 4.1506 | 4.0279 | 0.1227 |
| E2000111.00172A11 | 4.0455 | 9.0284 | 4.9829 | 4.1022 | 3.9829 | 0.1193 |
| E2000111.00172A12 | 4.0474 | 8.9949 | 4.9475 | 4.0979 | 3.9902 | 0.1077 |
| E2000111.00172A13 | 4.0632 | 9.0342 | 4.9710 | 4.1181 | 4.0047 | 0.1134 |
| E2000111.00172A18 | 4.0659 | 8.9378 | 4.8719 | 4.1128 | 4.002 | 0.1108 |
| | 24.3593 | | 29.7411 | 24.7036 | 24.0141 | |

TABLE 8

Gross retention in SYP blocks treated with ammoniacal solution of hydrolyzed styrene/maleic anhydride co-polymer complexed with copper.

| ID# | Dry wt (g) | Wet wt (g) | Gross Retention (g) | |
|---|---|---|---|---|
| E2000111.00172A1 | 4.1137 | 8.9459 | 4.8322 | |
| E2000111.00172A2 | 4.0574 | 8.3662 | 4.3088 | * |
| E2000111.00172A3 | 4.1159 | 8.2682 | 4.1523 | |
| E2000111.00172A4 | 4.1074 | 8.5934 | 4.4860 | |
| E2000111.00172A5 | 4.1219 | 8.4841 | 4.3622 | |
| E2000111.00172A6 | 4.0980 | 8.4226 | 4.3246 | |
| E2000111.00172A7 | 4.0554 | 9.0485 | 4.9931 | * |
| E2000111.00172A8 | 4.0819 | 9.0566 | 4.9747 | * |
| E2000111.00172A9 | 4.0255 | 9.0116 | 4.9861 | |
| E2000111.00172A10 | 4.1210 | 9.0059 | 4.8849 | |
| E2000111.00172A11 | 4.0455 | 9.0284 | 4.9829 | * |
| E2000111.00172A12 | 4.0474 | 8.9949 | 4.9475 | * |
| E2000111.00172A13 | 4.0632 | 9.0342 | 4.9710 | * |
| E2000111.00172A14 | 4.0345 | 8.9042 | 4.8697 | |
| E2000111.00172A15 | 4.0836 | 8.2797 | 4.1961 | |
| E2000111.00172A16 | 4.0391 | 9.0340 | 4.9949 | |
| E2000111.00172A17 | 4.0880 | 9.1013 | 5.0133 | |
| E2000111.00172A18 | 4.0659 | 8.9378 | 4.8719 | * |
| E2000111.00172A19 | 4.0614 | 9.0690 | 5.0076 | |
| E2000111.00172A20 | 4.0723 | 8.1971 | 4.1248 | |
| E2000111.00172A21 | 4.0264 | 8.3285 | 4.3021 | |
| E2000111.00172A22 | 4.0388 | 8.9164 | 4.8776 | |
| E2000111.00172A23 | 4.0601 | 8.5134 | 4.4533 | * |
| E2000111.00172A24 | 4.1043 | 8.8101 | 4.7058 | * |
| E2000111.00172A25 | 4.0556 | 8.3608 | 4.3052 | |
| E2000111.00172A26 | 4.0399 | 8.2314 | 4.1915 | |
| E2000111.00172A27 | 4.0112 | 9.1009 | 5.0897 | |
| E2000111.00172A28 | 4.0442 | 8.2796 | 4.2354 | |
| E2000111.00172A29 | 4.0291 | 9.0393 | 5.0102 | |
| E2000111.00172A30 | 4.0620 | 8.4588 | 4.3968 | |
| E2000111.00172A31 | 4.1368 | 8.8352 | 4.6984 | |
| E2000111.00172A32 | 4.0673 | 8.9195 | 4.8522 | * |
| | 130.1747 | | 149.4028 | |

* marks blocks having a gross retention falling within +/−5% of the group average C) Retention of Ammoniacal Solution of Hydrolyzed Styrene/Maleic Anhydride Copolymer and Copper Complex in Wood The 6 selected blocks in Example 2B were subjected to leaching as described in Example 1C. The results are given in Table 10. Six untreated control blocks were treated and leached as above and titrated with 0.00937 N thiosulfate to yield 0.000178 g of leachable copper background. This amount of copper was subtracted from the total amount of copper that was leached from the treated blocks (0.003294 g, Table 10) to give 0.003116 g of copper leached from the preservative. The amount of copper initially imbibed into the wood was 0.04417 g. Therefore only about 7.05%= [(0.003116/0.04417)(100)] of the copper leached out of the wood under these vigorous leaching conditions. This result shows that there is excellent retention of copper in the wood when it is complexed with hydrolyzed styrene/maleic anhydride copolymer.

After leaching, the blocks were weighed. Block weights (wt after leach test) are given in Table 9 above. This data shows that the blocks weigh slightly less after leaching.

TABLE 10

Leaching of copper from SYP blocks treated with ammoniacal solution of hydrolyzed styrene/maleic anhydride copolymer and copper complex.

| Hours | Vol. 0.00919N Thiosulfate | g Cu in leachate | Calculated g Cu remaining in blocks |
|---|---|---|---|
| 0 | 0.00 | 0.000000 | 0.044170 |
| 6 | 2.75 | 0.001604 | 0.042566 |
| 24 | 1.30 | 0.000758 | 0.041808 |
| 48 | 0.75 | 0.000438 | 0.041370 |
| 96 | 0.40 | 0.000233 | 0.041137 |
| 144 | 0.15 | 0.000087 | 0.041050 |
| 192 | 0.10 | 0.000058 | 0.040992 |
| 240 | 0.10 | 0.000058 | 0.040934 |
| 288 | 0.10 | 0.000058 | 0.040876 |
| 336 | 0.00 | 0.000000 | 0.040880 |
| 384 | 0.00 | 0.000000 | 0.040880 |
| Totals | 5.65 | 0.003294 | |

The remaining copper content of the blocks was analyzed by ashing. The blocks were allowed to dry at room temperature, then all 6 blocks were heated together at 250° C. for 2 hours, then at 580° C. for 18 hours. The amount of resulting ash and weight of initial wood sample are given in Table 11.

TABLE 11

Initial wood sample and ash weights.

| | |
|---|---|
| Wt of Crusible + lid + sample (g) | 115.6366 |
| Wt of Crusible + lid (g) | 91.6237 |
| Wt of sample (g) | 24.0129 |
| Wt of crusible + ash + lid (g) | 91.7647 |
| Wt of ash (g) | 0.141 |

The residue was analyzed for copper by adding 1 g of sulfuric acid and 50 ml of deionized water to the residue in a jar and continuing to follow the previously described titration procedure. By XRF, other metals such as manganese, iron, arsenic, and lead were found to be present in the ash. These metals were bound in the wood in such a fashion as not to be titratable in the leachate, but they were titratable by thiosulfate/iodide from the ash. The amount of copper in the ash, as determined by titration, was found to be 91.7% of the titratable metal content. By titration of the ash, the amount of copper that remained in the treated blocks after leaching was 0.0416 g. Thus by the ashing assay, 5.82% copper leached from the blocks (0.00257 g leached out of 0.044170 g initial). From the total ash of the 6 treated and leached blocks, 0.141 g of ash was obtained. By XRF analysis, the ash contained 28.27% copper or 0.0399 g of copper, resulting in a calculated loss of copper of 9.67%. The various methods of determining the percent copper leached from the blocks agree well with each other, since these methods of analysis are quite different. The results are given in Table 12.

TABLE 12

Comparison of copper loss calculations.

| Analysis Methods | % Cu lost |
|---|---|
| Titration of leachates | 7.05 |
| Titration of ashed blocks | 5.82 |
| XRF of ash | 9.67 |

C) Preparation and Environmental Testing of Fahlstrom Stakes Treated with Ammoniacal Solution of Hydrolyzed Styrene/Maleic Anhydride Copolymer and Copper Complex Selection and Preparation of Fahlstrom Stakes The following methods are based on AWPA Standard, Method E7-01, Sec. 4, 5, 6, and 7 and E11-97.

SYP boards, 3.175 cm×35.56 cm×243.84 cm (5/4"×14"×8 ft) and 3.175 cm×30.48 cm×243.84 cm (5/4"×12"×8 ft) were obtained from Delaware County Supply (Boothwin, Pa.). The boards were cut into Fahlstrom stakes of 4 mm×38 mm×254 cm (0.156"×1.5"×10") in size (AWPA Standard, Method E7-01, Sec 4.2, with the exception that the boards were milled without equilibration). The stakes were segregated by visual inspection (AWPA Standard, Method E7-01, Sec. 4.1) and stakes having knots, cracks, resin and sap pockets, signs of infection by mold, stain, and wood destroying fungi were eliminated. The remaining stakes were sorted into groups by weight (AWPA Standard, Method E7-01, Sec. 5). Stakes weighing between 20 g and 25 g were chosen for the imbibing experiment and placed in a controlled environment chamber at 23° C. and RH of 50% (Model 1-60LLVL Humidity Cabinet, Percival Scientific Inc., Boone, Iowa) for 21 days (AWPA Standard, Method E7-01, Sec. 4 and E11-97, Sec. 3). After equilibration in the environment chamber, each stake was identified by a painted number. Each stake was then weighed and dimensioned and the results recorded.

Treatment of the Fahlstrom stakes was carried out in a stainless steel pressure vessel designed and fabricated at the DuPont Experimental Station (Wilmington, Del.). Pressure was supplied by a Diaphragm Pump (Model S216J10; Sprague Products Div. of Curtiss-Wright Flow Control Corp., Brecksville, Ohio). The pressure vessel was constructed from sched. 80 SS pipe measuring 12.7 cm (5") diam. and was closed at each end with SS flanges and caps. The length of the pipe varied depending on the length of the wood to be treated. Typically, a 101.6 cm (40") length was chosen for treating 38" wood specimens. Other lengths of pipe were added via flanges to extend the length of the pressure vessel to accommodate 243.84 cm (8 ft) specimens or shorter lengths of pipe were used to treat 25.4 cm (10") specimens.

Batches of ten labeled stakes were loaded into a stainless steel separation rack (to simulate sticking, which is physical separation of lumber by placing small pieces of wood between boards to separate them, as well as two witness stakes (total 12 stakes), and placed in the pressure vessel. The pressure vessel was sealed and a vacuum of 69.85 cm Hg gauge (13.5 psig) was applied for a period of 30 minutes. The vacuum was broken by introduction of the imbibing fluid, the ammoniacal solution of hydrolyzed styrene/maleic anhydride copolymer copper salt prepared in Example 4A, to fill the pressure vessel and cover the wood. Air pockets were removed by circulating imbibing fluid through the vessel, and pressure of 7.18 kilopascal gauge (150 psig) was applied with a diaphragm pump for a period of 30 minutes. The pressure was released and the stakes allowed to equilibrate in the imbibing solution for 15 minutes. The pressure vessel was drained and the treatment rack bearing the stakes was removed. The stakes were lightly wiped with a paper towel and weighed. The Fahlstrom stakes gained weight in a manner similar to the stakes in Tables 1. and 2., which indicated that the ammoniacal solution of hydrolyzed styrene/maleic anhydride copolymer and copper complex was successfully imbibed into the wood.

The Fahlstrom stakes described were placed in the ground, as per AWPA E7-01, in Hialeah, Fla., Starke, Fla., Newark, Del., and LaPlace, La. Additional stakes treated with 1:2 and 1:4 dilutions of the same treatment solution were also placed in the ground at the same sites. In addition, untreated control stakes were placed in the ground at each location. The positioning of the stakes was randomized in the test sites as per AWPA E7-01. The stakes treated with the undiluted treatment solution in Hialeah, Fla. were evaluated for decay at 11, 17, and 23 months vs. untreated control stakes according to AWPA standard E7-01 and the results are given in Table 13. The treated stakes displayed much less fungal decay than the control stakes.

TABLE 13

Decay grading of Fahlstrom stakes treated with ammoniacal solution of hydrolyzed styrene/maleic anhydride copolymer and copper complex and tested in Hialeah, FL.

| Installed Sep. 21, 2004 Treatment | StakeID | Aug. 17, 2005 11 mo decay | Feb. 2, 2006 17 mo decay | Aug. 1, 2006 23 mo decay |
|---|---|---|---|---|
| 1485 ppm Cu/ | 199-04 | 10 | 10 | 9.5 |
| Hydrolyzed SMA | 199-09 | 10 | 10 | 9 |
| | 199-13 | 10 | 10 | 10 |
| | 199-14 | 10 | 10 | 9.5 |
| | 199-15 | 10 | 10 | 9.5 |

TABLE 13-continued

Decay grading of Fahlstrom stakes treated with ammoniacal solution of hydrolyzed styrene/maleic anhydride copolymer and copper complex and tested in Hialeah, FL.

Installed Sep. 21, 2004

| Treatment | StakeID | Aug. 17, 2005 11 mo decay | Feb. 2, 2006 17 mo decay | Aug. 1, 2006 23 mo decay |
|---|---|---|---|---|
| | 199-18 | 10 | 10 | 9 |
| | 199-21 | 10 | 10 | 9 |
| | 199-25 | 10 | 10 | 9.5 |
| | 199-36 | 10 | 10 | 9.5 |
| | 199-43 | 10 | 10 | 9 |
| | Avg | 10 | 10 | 9.35 |
| | SD | 0 | 0 | 0.32 |
| Untreated controls | 188-11 | 9 | 8 | 4 |
| | 188-12 | 0 | 0 | 0 |
| | 188-13 | 0 | 0 | 0 |
| | 188-14 | 0 | 0 | 0 |
| | 188-15 | 0 | 0 | 0 |
| | 188-16 | 9 | 9 | 4 |
| | 188-17 | 0 | 4 | missing |
| | 188-18 | 0 | 0 | 0 |
| | 188-19 | 0 | 0 | 0 |
| | 188-20 | 0 | 0 | 0 |
| | Avg | 1.8 | 2.1 | 0.89 |
| | SD | 3.79 | 3.42 | 1.66 |

Stakes treated with the undiluted and diluted solutions and tested at the Starke, Newark, and LaPlace sites were graded at the times listed in Table 14, and the averages of decay and insect results from these sites is compared to the averages from the Hialeah site at 17 months in Table 14.

TABLE 14

Averages of decay and insect damage gradings of Fahlstrom stakes treated with ammoniacal solution of hydrolyzed styrene/maleic anhydride copolymer and copper complex and tested at four sites.

| Location | Treatment:: Conc. in ppm | Time (Months) | Avg. Decay | Avg. Insect damage |
|---|---|---|---|---|
| Starke, FL | Cu1485/SMA Hydrolyzed | 18 | 9.4 | 10 |
| | Cu742/SMA Hydrolyzed | 18 | 8.7 | 9.7 |
| | Cu371/SMA Hydrolyzed | 18 | 9.1 | 8.9 |
| | Control | 18 | 4.8 | 4.4 |
| Newark, DE | Cu1485/SMA Hydrolyzed | 12 | 9.65 | 9.9 |
| | Cu742/SMA Hydrolyzed | 12 | 9.7 | 10 |
| | Cu371/SMA Hydrolyzed | 12 | 8.95 | 9.8 |
| | Control | 12 | 7.9 | 9.4 |
| Hialeah, FL | Cu1485/SMA Hydrolyzed | 17 | 10 | xxxx |
| L | Cu742/SMA Hydrolyzed | 17 | 9.1 | xxxx |
| | Cu371/SMA Hydrolyzed | 17 | 7.6 | xxxx |
| | Control | 17 | 2.1 | xxxx |
| LaPlace, LA | Cu1485/SMA Hydrolyzed | 7 | 9.9 | 10 |
| | Cu742/SMA Hydrolyzed | 7 | 9.6 | 10 |
| | Cu371/SMA Hydrolyzed | 7 | 9.2 | 10 |
| | Control | 7 | 8.9 | 9.9 | xxxx means no insect damage observed at that site.

With damage to controls extensive, strong protection by all treatment solutions was observed at the Hialeah and Starke, Fla. sites. There is little decay and insect damage at the Newark and LaPlace sites in 12 and 7 months, respectively. It is expected that over longer periods of time, treated decay stakes at the Newark and LaPlace sites will show less fungal attack and insect damage with respect to controls.

Example 5

Comparative Example

Copper/Cellulose Complex Insolubility in Ammoniacal Solution

The following experiment was done to show that not all polymers that form copper salts can be solubilized in ammonia water. As shown below, the resulting product was a viscid mass that could not be used to imbibe wood, so it could not be used as a wood preservative.

Into a 500 ml beaker was placed 250 g of water and 5 g of cellulose sulfate. The mixture was stirred and heated to boiling to dissolve the cellulose sulfate. The syrupy solution was cooled to room temperature and to it was added a solution prepared from 3.7 g of copper sulfate pentahydrate in 50 ml of water. A green viscous solution formed that was unsuitable for wood preservation because the copper salt of cellulose sulfate was soluble in water and would not fix to the wood. Then 3 ml of this solution was combined with 4 ml of conc. Ammonium hydroxide. A viscid mass resulted that, because of its insolubility in water, was unsuitable for pressure treatment of wood.

What is claimed is:

1. An aqueous composition comprising in admixture (a) a complex comprising (i) copper ions, zinc ions or a mixture thereof, and (ii) a hydrolyzed olefin/maleic anhydride copolymer having a molecular weight in the range of about 10,000 to about 50,000; and (b) ammonia and/or ethanolamine; wherein component (b) is present in an amount sufficient to solubilize the complex.

2. The composition of claim 1 wherein the copolymer is a hydrolyzed octene/maleic anhydride copolymer, a hydrolyzed styrene/maleic anhydride copolymer, or a mixture thereof.

3. The composition of claim 1 wherein component (b) comprises ammonia and ethanolamine.

4. The composition of claim 1 wherein the 10 000 to 50.000 molecular weight is weight average molecular weight.

5. The composition of claim 1 which further comprises a component (c) selected from one or both of an additional antifungal component and an additional termiticidal component.

6. The composition of claim 5 wherein the component (c) is selected from the group consisting of tungstate ion, molybdate ion, ibuprofen, a tropolone, and combinations thereof.

7. The composition of claim 5 wherein the component (c) comprises tungstate ion or molybdate ion.

8. A process for preserving cellulosic material, or an article that comprises cellulosic material, comprising contacting the cellulosic material or article with the composition of claim 1.

9. The process of claim 8 wherein the cellulosic material is selected from the group consisting of wood, lumber, plywood, oriented strand board, cellulose, hemicellulose, lignin, cotton, and paper.

10. The process of claim 8 which comprises dipping, brushing, spraying, draw-coating, rolling, or pressure-treating the cellulosic material or article with the composition of claim 1.

11. The process of claim 8 wherein the cellulosic material is wood or lumber.

12. The process of claim 11 further comprising subjecting wood or lumber to a vacuum before and/or after it is contacted with the composition.

13. The process of claim 8 further comprising a step of incorporating the cellulosic material or the article into a structure or into a consumable device.

14. Cellulosic material, or an article comprising a cellulosic material, wherein the composition of claim 1 is adsorbed on and/or absorbed in the cellulosic material.

15. The material or article of claim 14 wherein the cellulosic material is selected from the group consisting of wood, paper, cellulose, cotton, lignin, and hemicellulose.

16. The material or article of claim 14 wherein the copolymer is a hydrolyzed octene/maleic anhydride copolymer, a hydrolyzed styrene/maleic anhydride copolymer, or a mixture thereof.

17. The composition of claim 1 wherein the 10,000 to 50,000 molecular weight is number average molecular weight.

18. The material or article of claim 14 wherein the composition further comprises at least one component selected from the group consisting of tungstate ion, molybdate ion, ibuprofen, a tropolone, and combinations thereof.

19. The material or article of claim 14 wherein the composition further comprises tungstate ion or molybdate ion.

20. A structure or consumable device comprising the cellulosic material or article of claim 14.

* * * * *